US011402323B2

(12) United States Patent
Bowie et al.

(10) Patent No.: US 11,402,323 B2
(45) Date of Patent: Aug. 2, 2022

(54) SYSTEMS AND PROCESSES FOR PERFORMANCE PROPERTY DETERMINATION USING OPTICAL SPECTRAL DATA (71) Applicant: ExxonMobil Technology and Engineering Company, Annandale, NJ (US)

(72) Inventors: Bryan T. Bowie, Branchburg, NJ (US); John E. Lee, Spring, TX (US); Bryan E. Hagee, Hamilton, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 16/565,638

(22) Filed: Sep. 10, 2019

(65) Prior Publication Data
US 2020/0103340 A1    Apr. 2, 2020

Related U.S. Application Data (60) Provisional application No. 62/740,032, filed on Oct. 2, 2018.

(51) Int. Cl.
*G01N 21/3577* (2014.01)
*G01N 33/28* (2006.01)
*G01N 21/35* (2014.01)

(52) U.S. Cl.
CPC ..... *G01N 21/3577* (2013.01); *G01N 33/2829* (2013.01); *G01N 2021/3595* (2013.01); *G01N 2201/129* (2013.01)

(58) Field of Classification Search
CPC .......... G01N 21/3577; G01N 33/2829; G01N 2021/129; G01N 2021/3595; C10G 2300/1059; G16C 20/30
(Continued)

(56) References Cited

U.S. PATENT DOCUMENTS 6,662,116 B2    12/2003  Brown
7,904,251 B2     3/2011  Martin et al.
(Continued)

OTHER PUBLICATIONS

Baldrich Ferrer, et al; "Infrared Spectrophotometry, A Rapid and Effective Tool for Characterization of Direct Distillation Naphthas"; Ciencia Tecnologia y Future; 2005; vol. 3 No. 1; pp. 25-33.
(Continued)

*Primary Examiner* — Michael P Nghiem
(74) *Attorney, Agent, or Firm* — Vorys, Sater, Seymour and Pease LLP (57) ABSTRACT

Systems and methods for determining performance properties of an unknown composition are disclosed. The performance properties can include a Research Octane Number (RON), a Motor Octane Number (MON), and/or a cetane number. The systems and methods include utilizing an optical spectrum of an unknown composition to determine a model of composition, where the model of composition includes a molecular identity and a relative abundance for components therein. The model of composition is then utilized to calculate one or more performance properties. Additionally, the fit quality for the model of composition is determined by performing a partial least squares analysis on specific spectral regions of interest in the optical spectra of the unknown composition.

7 Claims, 2 Drawing Sheets

(58) Field of Classification Search
USPC .......................................................... 702/30
See application file for complete search history.

(56) References Cited

U.S. PATENT DOCUMENTS

| | | | |
|---|---|---|---|
| 8,322,200 | B2 | 12/2012 | Brown et al. |
| 8,682,597 | B2 | 3/2014 | Brown et al. |
| 2017/0023538 | A1* | 1/2017 | Mertens ................ G01N 21/31 |
| 2017/0190991 | A1* | 7/2017 | Sundberg .............. C10G 11/00 |
| 2018/0134978 | A1* | 5/2018 | Choi ....................... C10L 1/06 |
| 2020/0103390 | A1* | 4/2020 | Bowie .................... G06F 17/17 |

OTHER PUBLICATIONS

Marinovic, et al; "Prediction of Diesel Fuel Properties by Vibrational Spectroscopy Using Multivariate Analysis"; Journal of Analytical Chemistry; 2012, vol. 67 No. 12; pp. 939-949.

Goicoechea, et al; "A New Family of Genetic Algorithms for Wavelength Interval Selection in Multivariate Analytical Spectroscopy"; Journal of Chemometrics; 2003; vol. 17; pp. 338-345.

Cramer, et al; "Automated Wavelength For Spectroscopic Fuel Models by Symmetrically Contracting Repeated Unmoving Window Partial Least Squares"; Elsevier B.V.; 2008; vol. 92; pp. 13-21.

The International Search Report and Written Opinion for PCT/US2019/050292 dated Dec. 2, 2019.

Ghosh, et al., "Development of a Detailed Gasoline Composition-Based Octane Model", Ind. Eng. Chem. Res., 2006, vol. 45, pp. 337-345.

Ghosh, et al., "Detailed Composition-Based Model for Predicting the Cetane Number of Diesel Fuels", Ind. Eng Chem. Res., 2006, vol. 45, pp. 346-351.

* cited by examiner

SYSTEMS AND PROCESSES FOR PERFORMANCE PROPERTY DETERMINATION USING OPTICAL SPECTRAL DATA

CROSS REFERENCE TO RELATED APPLICATIONS

This application claims priority to U. S. Provisional Application Ser. No. 62/740,032 filed Oct. 2, 2018, which is herein incorporated by reference in its entirety.

FIELD

Systems and processes for determining performance properties using optical spectral data are provided.

BACKGROUND

Various processes have been utilized to model performance properties of petroleum distillate fractions, such as naphtha boiling range compositions, diesel boiling range compositions, or jet fuel boiling range compositions. Certain methods attempt to determine a Research Octane Number (RON), a Motor Octane Number (MON), and/or a cetane number from such petroleum distillate fractions by utilizing bulk property measurement, while other methods utilize spectral information of the fraction. However, such methods that utilize bulk property measurements can be resource intensive, while methods that utilize spectral information can be imprecise, due to the complex relationship between performance properties and optical spectra. It would be desirable to develop processes and systems for reliably determining performance properties of unknown petroleum distillate fractions using optical spectral data.

U.S. Pat. No. 6,662,116 describes a method of determining a property of an unknown material using an IR spectrum by fitting the IR spectrum to a linear combination of known spectra in a database.

U.S. Pat. No. 7,904,251 describes a method for modifying a synthetically generated assay of a whole crude oil, such as a condensate or resid material, by using measured crude properties.

U.S. Pat. No. 8,322,200 describes a method of analyzing that a manufactured product, e.g., a composition, meets regulatory and/or contractual requirements. The analysis is performed by re-introducing a manually or automatically collected sample that is representative of the manufactured product back into the one or more on-line process analyzers.

U.S. Pat. No. 8,682,597 describes a method for determining the composition of a material by fitting multivariate analytical data of an unknown whole crude to a database of multivariate analytical data of known whole crudes to provide an initial estimate of the composition. The method further includes refining the initial estimate of the composition by matching a set of additional analytical data.

SUMMARY

In one aspect, a method for estimating a performance property of a naphtha boiling range composition is provided. The method can include representing an optical spectrum of a first naphtha boiling range composition as a first weighted combination of optical spectra from a library of optical spectra. The method can also include generating a model of composition for the first naphtha boiling range composition based on the first weighted combination of optical spectra. Additionally, the method can include estimating a RON, MON, or both based on the model of composition.

In another aspect, a method for determining a performance property of a diesel boiling range composition is provided. The method can include representing an optical spectrum of a first diesel boiling range composition as a first weighted combination of optical spectra from a library of optical spectra. The method can also include generating a model of composition for the first diesel boiling range composition based on the first weighted combination of optical spectra. Further, the method can include estimating a cetane number based on the model of composition.

In yet another aspect, a method for determining a performance property of a jet fuel boiling range composition is provided. The method can include representing an optical spectrum of a first jet fuel boiling range composition as a first weighted combination of optical spectra from a library of optical spectra. The method can also include generating a model of composition for the first jet fuel boiling range composition based on the first weighted combination of optical spectra. Additionally, the method can include estimating a cetane number based on the model of composition.

DETAILED DESCRIPTION

Overview

In various aspects, processes and systems are provided for utilizing an optical spectrum of an unknown composition, e.g., a petroleum naphtha fraction and/or distillate fraction, to calculate one or more performance properties, such as a Research Octane Number (RON), a Motor Octane Number (MON), and/or a cetane number. In aspects, the optical spectrum of the unknown composition is approximated as a weighted combination of optical spectra of known compositions from a database. In such aspects, since the compositional profile of the compositions from the database is known, this weighted combination is utilized to form a model of composition for the unknown composition, based on its optical spectrum. This model of composition may include the compositional profile, e.g., the relative abundance and identity of the components, which is then utilized to calculate the performance properties, e.g., RON, MON, cetane number or a combination thereof. In further aspects, a fit quality may be determined for the model of composition that can provide an indication of the confidence in the model of composition and in the calculated performance properties.

Certain methods have been developed to attempt to determine RON, MON, or cetane directly from an optical spectrum of an unknown composition. However, such methods have failed to accurately determine performance properties because the performance properties are not linear with respect to the concentration of the molecular composition. Further, such methods are not transferrable to use at multiple refineries, where the chemical slate is often different, in turn, changing the model space.

The processes and systems described herein can alleviate one or more of the problems mentioned above. As noted above, it is difficult to predict performance properties from optical spectra of an unknown composition. The processes and systems described herein can overcome this issue by representing an optical spectrum of an unknown composition as a weighted combination of spectra of known compositions to generate a model of composition, and then utilize this model of composition to calculate performance properties. In one aspect, the systems and processes described herein provide a technical effect of allowing an operator to determine performance properties of an unknown composition from an optical spectrum, by first using the spectrum to determine a model of composition.

In aspects, an optical spectrum of an unknown composition, such as a naphtha boiling range composition, a jet fuel boiling range composition, or a diesel boiling range composition is obtained. In such aspects, this optical spectrum of an unknown composition can be represented as a weighted combination of spectra from a library of optical spectra of known compositions to determine a model of composition for the unknown composition. For instance, in one example, a Fourier Transform Infrared (FT-IR) spectrum of an unknown naphtha boiling range composition can be represented as a linear combination of a library of FT-IR spectra of known naphtha boiling range compositions to determine a linear combination of the known spectra that approximate the unknown spectrum. The coefficients from this linear combination of known spectra are then utilized to calculate the model of composition, which includes the compositional profile and relative abundance of each component. In aspects, this model of composition can then be utilized to calculate performance properties, such as RON and/or MON using various conventional techniques.

In aspects, a model of composition using a linear combination of FT-IR spectra from known compositions, may not indicate to an operator if this prediction has good fit quality for specific spectral regions of interest and/or for specific classes of compounds of interest. Rather the fit parameters typically generated with such a model of composition relate to the entire spectrum, which may or may not be relevant to a specific wavelength region of interest or for various compound classes of interest.

Optionally, a fit quality of the model of composition can be determined in order to provide the operator with an indication of whether or not the database of known FT-IR spectra (or other spectra) adequately represent spectral sub-regions of interest in the optical spectrum of the unknown composition. Such a fit quality indication can be valuable when utilizing these processes at multiple refineries or after slate changes, where unknown compositions may be substantially different. In one aspect, a technical effect of the fit quality determination is to provide this indication of fit quality for the model of composition, so that the operator can rely on the model of composition being utilized to determine the performance properties.

In determining the fit quality, partial representations of specific spectral regions of interest from the FT-IR spectrum of the unknown composition can be determined, which can include weighted combinations of spectra from known compositions to approximate this specific spectral region of interest. Partial least squares (PLS) analysis can be performed to give error statistics (leverage, residual, and/or distance) specific to those regions of interest. In some aspects, the specific wavelength regions of interest can correlate with specific classes of compounds, e.g., n-paraffins, iso-paraffins, naphthenes, olefins, total aromatics, or one-, two, three-, or four-ring aromatics.

In various aspects, the PLS statistics, e.g., leverage, residual, and/or distance, of one or more spectral regions of interest can be weighted to give an increased level of importance to the overall analysis, e.g., a specific regression model on naphtha spectra and olefins. The combined error or weighted combined error statistics, generated from these specific models can be used to give the fit quality for the model of composition. An indication that such a model is a good fit provides an enhanced, more meaningful level of confidence in the model of composition and the resulting calculated performance properties. An indication that such a model is not a good fit indicates that alternative, more laborious conventional assays may be required for calculating the performance properties.

In this discussion, unless otherwise specified, a "naphtha boiling range composition" refers to a composition that exhibits an initial or T5 boiling point of at least about 50° F. (10° C.), and a final or T95 boiling point of 350° F. (177° C.).

In this discussion, unless otherwise specified, a "light naphtha boiling range composition" refers to a composition that exhibits an initial or T5 boiling point of at least about 50° F. (10° C.), and a final or T95 boiling point of 250° F. (121° C.).

In this discussion, unless otherwise specified, a "heavy naphtha boiling range composition" refers to a composition that exhibits an initial or T5 boiling point of at least about 200° F. (93° C.), and a final or T95 boiling point of 400° F. (204° C.).

In this discussion, unless otherwise specified, "jet fuel boiling range composition" refers to a composition that exhibits an initial or T5 boiling point of at least about 284° F. (140° C.), and/or a final or T95 boiling point of less than about 572° F. (300° C.).

In this discussion, unless otherwise specified, "diesel boiling range composition" refers to a composition that exhibits an initial or T5 boiling point of at least about 350° F. (177° C.), and/or a final or T95 boiling point of less than about 650° F. (343° C.).

In this discussion, unless otherwise specified, "distillate fuel" refers to a distillate fraction that includes, but is not limited to, a diesel boiling range composition and a jet fuel boiling range composition.

In this discussion, unless otherwise specified, "T5 boiling point" refers to a temperature at which 5 wt. % of the feed, effluent, product, stream, or composition of interest will boil. In this discussion, unless otherwise specified, "T95 boiling point" refers to a temperature at which 95 wt. % of the feed, effluent, product, stream, or composition of interest will boil.

Generation of a Model of Composition

As discussed above, in aspects, a model of composition can be determined for an FT-IR spectrum of an unknown composition utilizing a library of FT-IR spectra from known compositions. While the present discussion references FT-IR spectra, it should be understood that FT-IR is just one example of optical spectra that can be utilized in the present invention, and that other types of optical spectroscopy that can be correlated with compositional information can be used, such as Ultraviolet-visible spectroscopy (UV-vis) and Raman spectroscopy. Further as mentioned above, the unknown composition for determining performance properties can be a naphtha boiling range composition, a light naphtha boiling range composition, a heavy naphtha boiling range composition, a jet fuel boiling range composition, or a diesel boiling range composition.

In various aspects, a model of composition can be determined using (1) multivariate analytical techniques such as FT-IR alone, or in combination with a small set of appropriately chosen property measurements of the sample whose composition is sought, (2) a library (database) of similar samples that have measured multivariate analytical data (e.g., FT-IR), measured HDHA and measured properties and (3) an optimization algorithm as referenced below which constructs the reference composition for the sample as a blend of similar samples in the library so that the multivariate (FT-IR) and property data for the blend is consistent with the multivariate (FT-IR) data and property made on that sample. The synthesis algorithm is then applied to adjust the reference composition to meet known properties of the unknown sample. This method is used to estimate assay data for the unknown composition based on the calculated blend and the assay data of the known compositions. This method is described in detail in U.S. Pat. No. 6,662,116, the entire contents of which are incorporated herein by reference.

If the FT-IR spectrum is used alone, then the analysis involves the minimization of the difference between the FT-IR spectrum of the unknown and that calculated as the linear combination of the FT-IR spectra of the blend of the reference samples. See equations (1) and (2) below.

$$\min((\hat{x}_u - x_u)^T(\hat{x}_u - x_u)) \quad (1)$$

$$\hat{x}_u = Xc_u \quad (2)$$

$x_u$ is a column vector containing the FT-IR for the unknown crude, and X is the matrix of FT-IR spectra of the reference crudes. The FT-IR spectra are measured on a constant volume of crude oil, so they are blended on a volumetric basis. Both $x_u$ and X are orthogonalized to corrections (baseline polynomials, water vapor spectra, and liquid water spectra) as described in U.S. Pat. No. 6,662,116.

To ensure that the composition calculated is non-negative, the minimization is conveniently done using a non-negative least squares. The analysis provides coefficients for a linear combination of the reference crudes that most closely matches (in a least squares sense) the spectrum of the unknown crude.

The coefficients from this linear combination of known spectra is then utilized to calculate the model of composition, which includes the compositional profile and relative abundance of each component.

Fit Quality Determination for the Predicted Model of Composition

In aspects, a model of composition using a linear combination of FT-IR spectra from known compositions, does not indicate to an operator if this prediction has good fit quality for specific spectral regions of interest and/or for specific classes of compounds of interest. Rather the fit parameters typically generated with such a model of composition relate to the entire spectrum, which may or may not be relevant to a specific wavelength region of interest or for various compound classes of interest.

In aspects, to determine the fit quality, one or more spectral regions of interest of the FT-IR spectrum of the unknown composition, which may be associated with one or more compositional classes, are utilized to determine if such compositional classes are adequately represented in the database of FT-IR spectra of known compositions. In such aspects, a weighted combination of FT-IR spectra from the database of known compositions is utilized to determine a partial representation of the FT-IR spectral region of interest associated with a compositional class, e.g., n-paraffins, iso-paraffins, naphthenes, olefins, total aromatics, or one-, two-, three-, or four-ring aromatics. As discussed further below, in aspects, the resulting PLS values, e.g., combined leverage and/or combined residual, can be utilized to determine the fit quality for the model of composition As mentioned above, in various aspects, the specific wavelength regions of interest may correlate with specific classes of compounds, e.g., n-paraffins, iso-paraffins, naphthenes, total aromatics, or one-, two, three-, or four-ring aromatics. In one aspect, the n-paraffins can be associated with a wavelength region or regions of: about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof. In one aspect, the iso-paraffins can be associated with a wavelength region or regions of: about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof. In various aspects, total naphthenes can be associated with a wavelength region or regions of: about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof. In various aspects, total aromatics can be associated with a wavelength region or regions of: about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof. In aspects, one-ring aromatics (ARC1) can be associated with a wavelength region or regions of: about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof. In aspects, two-ring aromatics (ARC2) can be associated with a wavelength region or regions of: about 900 $cm^{-1}$ to about 1300 $cm^{-1}$, about 1550 $cm^{-1}$ to about 1750 $cm^{-1}$, about 2700 $cm^{-1}$ to about 3000 $cm^{-1}$, about 3000 $cm^{-1}$ to about 3200 $cm^{-1}$, or a combination thereof. In certain aspects, three-ring aromatics (ARC3) can be associated with a wavelength region or regions of: about 1000 $cm^{-1}$ to about 1100 $cm^{-1}$, about 1500 $cm^{-1}$ to about 1700 $cm^{-1}$, about 3000 $cm^{-1}$ to about 4500 $cm^{-1}$, or a combination thereof. In aspects, four-ring aromatics (ARC4) can be associated with a wavelength region or regions of: about 900 $cm^{-1}$ to about 1000 $cm^{-1}$, about 1100 $cm^{-1}$ to about 1200 $cm^{-1}$, about 1300 $cm^{-1}$ to about 1500 $cm^{-1}$, about 1650 $cm^{-1}$ to about 1850 $cm^{-1}$, about 3100 $cm^{-1}$ to about 3300 $cm^{-1}$, about 4100 $cm^{-1}$ to about 4400 $cm^{-1}$, or a combination thereof.

In certain aspects, when the unknown composition is a naphtha boiling range composition, light naphtha boiling range composition, and/or a heavy boiling range composition, an operator may be most interested in determining the fit quality of wavelength sub-regions associated with olefins, n-paraffins, and/or iso-paraffins. In various aspects, when the known composition is a diesel boiling range composition or jet fuel boiling range composition, an operator may be most interested in determining the fit quality of wavelength sub-regions associated with n-paraffins, iso-paraffins, and/or aromatics.

In various aspects, one or more spectral regions of interest (which correspond to classes of compounds) can be utilized in the fit quality determination. In such aspects, for each spectral region of interest, a weighted combination of FT-IR spectra from known compositions is determined as a partial representation of the spectral region of interest. Further, as discussed above, a leverage and/or residual value can be determined for each of these partial representations. Leverage and/or residual values from two or more of these partial representations can be combined to determine a combined leverage value and/or a combined residual value, as described in the below PLS statistical equations.

In aspects, a conventional PLS model of combined residual ($FQR_{residual}$) can be utilized, such as that identified below in equation (3), in order to identify the cumulative difference between a fitted line and the corresponding data points from the sub-regions of interest in the FT-IR spectrum of the unknown sample.

$$FQR_{residual}=(R_{residual}*W_{weights\ residual}*R^T_{residual})/(90\%CI) \quad (3)$$

In this equation (3) the $R_{residual}$ is as defined in equation (4) below, the $W_{weights\ residual}$ is as defined in equation (5) below, and the $R^T_{residual}$ is an the transpose residual of equation (4). 90% CI refers to the 90% confidence interval.

In equation (4) below, the residual is from a pooled value the residuals determined for each sub-region of interest that were queried in this PLS analysis.

$$R_{residual}=R_{n-p},R_{i-p},R_N,R_o,R_{ARC1},R_{ARC2},R_{ARC3},R_{ARC4}, \quad (4)$$

$R_{n-p}$ refers to the residual of the total n-paraffins, $R_{i-p}$ refers to the residual of the total iso-paraffins, $R_o$ refers to the residual of the total olefins, $R_N$ refers to the residual of the total naphthenes, $R_{ARC1}$ refers to the residual of the total one-ring aromatics, $R_{ARC2}$ refers to the residual of the total two-ring aromatics, $R_{ARC3}$ refers to the residual of the total three-ring aromatics, and $R_{ARC4}$ refers to the residual of the total four-ring aromatics.

In equation (5) below, the individual esiduai values form equation (4) can be individually weighted to provide enhance importance to particular sub-regions of interest, as shown in equation (5) below.

$$W_{weights\ residual}=Wr_{n-p},We_{i-p},Wr_N,Wr_o,Wr_{ARC1},Wr_{ARC2},Wr_{ARC3},Wr_{ARC4} \quad (5)$$

$Wr_{n-p}$ refers to the weighted residual of the total n-paraffins, $Wr_{i-p}$ refers to the weighted residual of the total iso-paraffins, $Wr_N$ refers to the weighted residual of the total naphthenes, $Wr_o$ refers to the weighted residual of the total olefins, $Wr_{ARC1}$ refers to the weighted residual of the total one-ring aromatics, $Wr_{ARC2}$ refers to the weighted residual of the total two-ring aromatics, $Wr_{ARC3}$ refers to the weighted residual of the total three-ring aromatics, and $Wr_{ARC4}$ refers to the weighted residual of the total four-ring aromatics. In aspects, the residual of each individual class of compositions or sub-regions that were queried can be weighted differently from one another.

In aspects, a conventional PLS model of combined leverage ($FQR_{leverage}$) can be utilized, such as that identified below in equation (6), in order to provide a combined measure of data points from the sub-regions of interest in the unknown composition spectrum that are outside the data points in the library of known composition spectra.

$$FQR_{leverage}=(L_{deverage}*W_{weights\ leverage}*L^T_{leverage})/(90\%CI) \quad (6)$$

In this equation (6) the $L_{leverage}$ is as defined in equation (7) below, the $W_{weights\ leverage}$ is as defined in equation (8) below, and the $L^T_{leverage}$ is an the transpose leverage of equation (7). 90% CI refers to the 90% confidence interval.

In equation 7 below, the $L_{leverage}$ is a pooled value from the leverage determined for each sub-region of interest that were queried in this PLS analysis.

$$L_{leverage}=L_{n-p},L_{i-p},L_N,L_o,L_{ARC1},L_{ARC2},L_{ARC3},L_{ARC4} \quad (7)$$

$L_{n-p}$ refers to the leverage of the total n-paraffins, $L_{i-p}$ refers to the leverage of the total iso-paraffins, $L_N$ refers to the leverage of the total naphthenes, $L_o$ refers to the leverage of the total olefins, $L_{ARC1}$ refers to the leverage of the total one-ring aromatics, $L_{ARC2}$ refers to the leverage of the total two-ring aromatics, $L_{ARC3}$ refers to the leverage of the total three-ring aromatics, and $L_{ARC4}$ refers to the leverage of the total four-ring aromatics.

In equation (8) below, the individual $L_{leverage}$ values from equation (7) can be individually weighted to provide enhance importance to particular sub-regions of interest, as shown in equation (8) below.

$$W_{weights\ leverage}=Wl_{n-p},Wl_{i-p},Wl_N,Wl_o,Wl_{ARC1},Wl_{ARC2},Wl_{ARC3},Wl_{ARC4} \quad (8)$$

$Wl_{n-p}$ refers to the weighted leverage of the total n-paraffins, $Wl_{i-p}$ refers to the weighted leverage of the total iso-paraffins, $Wl_N$ refers to the weighted leverage of the total naphthenes, $Wl_o$ refers to the weighted leverage of the total olefins, $Wl_{ARC1}$ refers to the weighted leverage of the total one-ring aromatics, $Wl_{ARC2}$ refers to the weighted leverage of the total two-ring aromatics, $Wl_{ARC3}$ refers to the weighted leverage of the total three-ring aromatics, and $Wl_{ARC4}$ refers to the weighted leverage of the total four-ring aromatics. In aspects, the leverage of each individual class of compositions or sub-regions that were queried can be weighted differently from one another.

As discussed above, when the combined residual ($FQR_{residual}$) is one or less and/or when the combined leverage ($FQR_{leverage}$) is one or less can indicate that the model composition is a good fit. Since the operator can pick which wavelength regions of interest to develop cumulative error statistics of the model of composition, an indication that such a model is a good fit provides an enhanced, more meaningful level of confidence in the model of composition. For example, in aspects, when the combined residual and/or combined leverage are one or less, this means the model of composition is a good fit for the particular spectral regions of interest, or classes of compounds of interest.

In various aspects, a combined leverage above one or a combined residual above one can indicate that the model of composition is not a good fit. That is, such PLS statistical value(s) can indicate that the FT-IR spectral library of known compositions does not adequately represent spectral regions of interest (corresponding to classes of compounds) in the unknown composition. For instance, if the residual or the leverage value is above one with respect to olefins and iso-paraffins, then the FT-IR spectral library of known compositions does not adequate represent olefins and iso-paraffins. In such an instance, since the predicted model of composition may not be a good fit, the operator may consider alternative more laborious conventional models for determining the performance properties of the unknown composition.

Optionally or alternatively, a distance PLS statistical value can be calculated to provide or refine fit quality information of the predicted model of composition. A conventional PLS distance calculation is shown in equation (9) below.

$$D_{distance}=\sqrt{FQR_{residual}^2+FQR_{leverage}^2} \quad (9)$$

As can be seen in equation (9) above, this distance calculation can provide a single statistical value that combines the combined leverage and combined residual values discussed above. In this aspect, the single distance value can provide an alternative fit quality measurement which takes into account the relative strength of the combined leverage and combined residual. For example, by determining a single value fit quality, this allows an operator to determine if a favorable combined leverage, e.g., a value at or below one, can offset an unfavorable combined residual, e.g., a value above one. In another example, this single value distance analysis allows an operator to determine if a favorable combined residual, e.g., a value at or below one, can offset an unfavorable combined residual, e.g., a value above one.

In certain aspects, the distance value itself can be utilized to determine the fit quality of the model of composition. In such aspects, if the distance value is about one or less, this can indicate that the fit quality is acceptable, whereas if the distance value is more than one, this can indicate that the fit quality is unacceptable.

Determining Performance Properties of the Model of Composition

The model of composition, as determined according to the above processes, may include the compositional profile, e.g., the relative abundance and identity of the components, which allows for calculating the performance properties. For example, in aspects, once the model of composition has been determined, and the fit quality of this model is determined to be adequate, various performance properties can be calculated, such as RON, MON, and/or cetane.

In certain aspects, when the unknown composition is a naphtha boiling range composition, a light naphtha boiling range composition, or a heavy boiling range naphtha composition, the RON and/or MON can be determined. In aspects, any convenient method can be utilized to determine the RON and/or MON, such as that described in Ghosh et al., "Development of a Detailed Gasoline Composition-Based Octane Model," *Ind. Eng. Chem. Res.* 2006, 45, 337-345.

In various aspects, when the unknown composition is a diesel boiling range composition or a jet fuel boiling range composition, the cetane number can be determined. In aspects, any convenient method can be utilized to determine the cetane number, such as that described in Ghosh et al., "Detailed Composition-Based Model for Predicting the Cetane Number of Diesel Fuels," *Ind. Eng. Chem. Res.* 2006, 45, 346-351.

Figure 1:
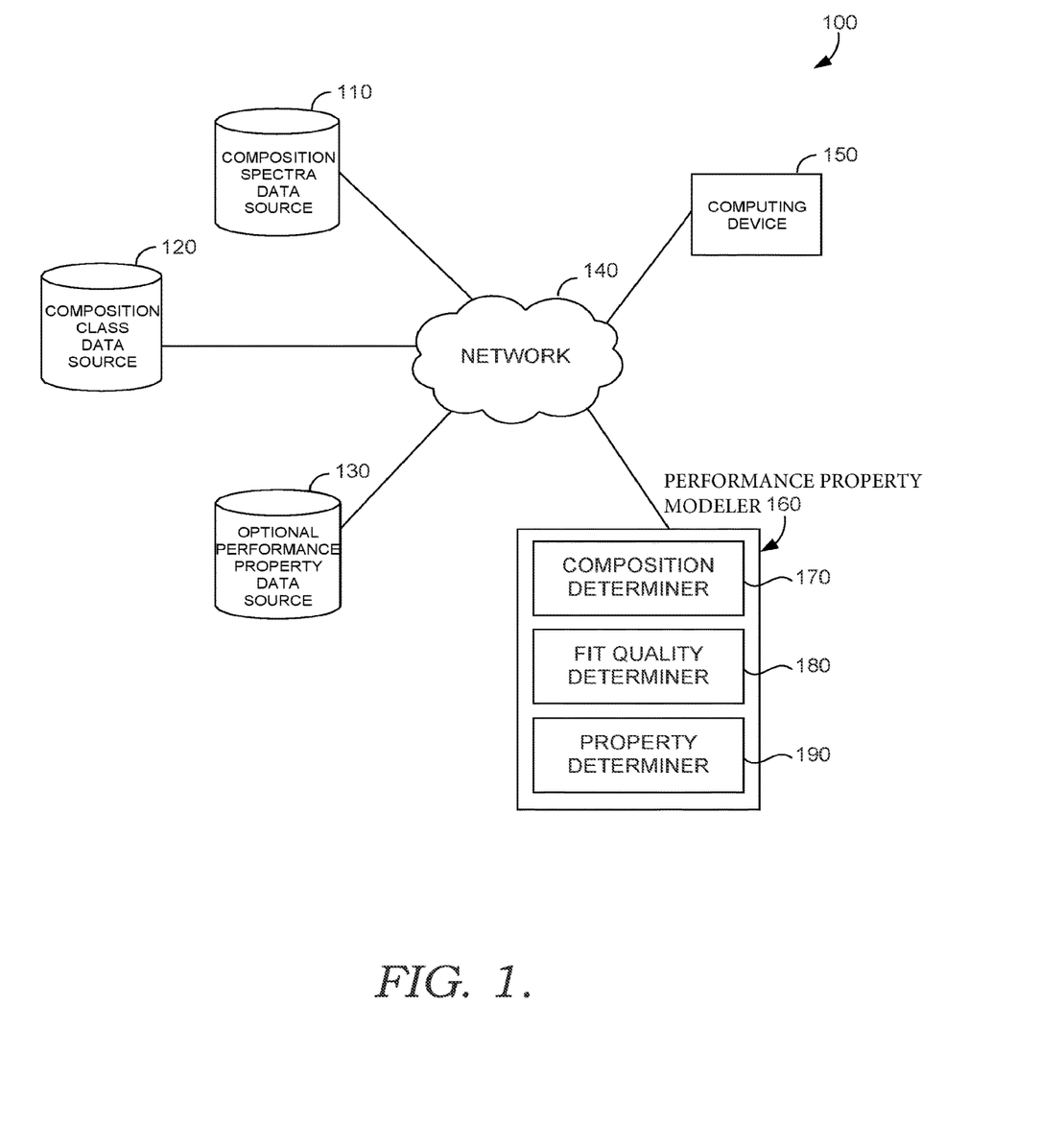
FIG. 1 shows a block diagram of a system for determining performance properties of a petroleum distillate fraction.

Example System for Determining Performance Properties Based on Optical Spectral Data FIG. 1 is one example of a system 100 that can be utilized to determine the performance properties of an unknown composition. It should be understood that the system 100 is an example of one suitable computing system environment and is not intended to suggest any limitation as to the scope of use or functionality of aspects of the present invention. Neither should the system 100 of FIG. 1 be interpreted as having any dependency or requirement related to any single source module, service, or device illustrated therein.

Generally, the system 100 can include a performance property modeler 160. The performance property modeler 160 can determine a model of composition of an unknown composition using an optical spectrum of the unknown sample, determine the fit quality of the model of composition, and determine one or more performance properties of the unknown composition, based on the model of composition.

The system 100 may include the performance property modeler 160, a known composition spectra data source 110, compositional class data source 120, an optional performance property data source 130, and a computing device 150. In aspects, the performance property modeler 160, the known composition spectra data source 110, the compositional class data source 120, the performance property data source 130, and a computing device 150 all may be in communication with each other, through wired or wireless connections, and/or through a network 140. The network 140 may include, without limitation, one or more local area networks (LANs) and/or wide area networks (WANs). Such networking environments are commonplace in enterprise-wide computer networks, intranets, and the Internet. Accordingly, the network 140 is not further described.

In one or more aspects, the known composition spectra data source 110 can include optical spectra, e.g., FT-IR spectra, of known compositions. In such aspects, these known compositions can refer to compositions having a compositional profile, e.g., the relative abundance and identity of the components in the composition. In certain aspects, the known composition spectra data source 110 can include individual FT-IR spectra of at least about 50, at least about 100, or at least about 300 known compositions. In the same or alternative aspects, the known composition spectra data source 110 can include FT-IR spectra derived from compositions at different refineries and/or from different crudes.

In aspects, the compositional class data source 120 can include information on specific regions of FT-IR spectra that may be of interest to an operator. In one aspect, the compositional class data source 120 can include FT-IR spectral regions associated with n-paraffins, iso-paraffins, naphthenes, total aromatics, or one-, two-, three-, or four-ring aromatics, or combinations thereof. As discussed above, in one aspect, the n-paraffins can be associated with a wavelength region or regions of: about 1350 cm$^{-1}$ to about 1550 cm$^{-1}$, about 2750 cm$^{-1}$ to about 3000 cm$^{-1}$, about 4000 cm$^{-1}$ to about 4600 cm$^{-1}$, about 5400 cm$^{-1}$ to about 6000 cm$^{-1}$, or a combination thereof. In one aspect, the iso-paraffins can be associated with a wavelength region or regions of: about 900 cm$^{-1}$ to about 1200 cm$^{-1}$, about 1300 cm$^{-1}$ to about 1600 cm$^{-1}$, about 2600 cm$^{-1}$ to about 3000 cm$^{-1}$, about 4000 cm$^{-1}$ to about 4600 cm$^{-1}$, or a combination thereof. In various aspects, total naphthenes can be associated with a wavelength region or regions of: about 1450 cm$^{-1}$ to about 1550 cm$^{-1}$, about 2500 cm$^{-1}$ to about 3000 cm$^{-1}$, about 4000 cm$^{-1}$ to about 4600 cm$^{-1}$, or a combination thereof. In various aspects, total aromatics can be associated with a wavelength region or regions of: about 800 cm$^{-1}$ to about 1300 cm$^{-1}$, about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof. In aspects, one-ring aromatics (ARC1) can be associated with a wavelength region or regions of: about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof. In aspects, two-ring aromatics (ARC2) can be associated with a wavelength region or regions of: about 900 cm$^{-1}$ to about 1300 cm$^{-1}$, about 1550 cm$^{-1}$ to about 1750 cm$^{-1}$, about 2700 cm$^{-1}$ to about 3000 cm$^{-1}$, about 3000 cm$^{-1}$ to about 3200 cm$^{-1}$, or a combination thereof. In certain aspects, three-ring aromatics (ARC3) can be associated with a wavelength region or regions of: about 1000 cm$^{-1}$ to about 1100 cm$^{-1}$, about 1500 cm$^{-1}$ to about 1700 cm$^{-1}$, about 3000 cm$^{-1}$ to about 4500 cm$^{-1}$, or a combination thereof. In aspects, four-ring aromatics (ARC4) can be associated with a wavelength region or regions of: about 900 cm$^{-1}$ to about 1000 cm$^{-1}$, about 1100 cm$^{-1}$ to about 1200 cm$^{-1}$, about 1300 cm$^{-1}$ to about 1500 cm$^{-1}$, about 1650 cm$^{-1}$ to about 1850 cm$^{-1}$, about 3100 cm$^{-1}$ to about 3300 cm$^{-1}$, about 4100 cm$^{-1}$ to about 4400 cm$^{-1}$, or a combination thereof.

In various aspects, the compositional class data source 120 can also include one or more FT-IR spectra of unknown compositions in order to identify specific spectral of interest for use in the fit quality determination.

In various aspects, the optional performance property data source 130 can include information for calculating the performance property from the model of composition, such as information related to performance properties of specific compounds or classes of compounds.

In various aspects, the performance property modeler 160 can include a composition determiner 170, a fit quality determiner 180, and property determiner 190. In aspects, one or more of the composition determiner 170, the fit quality determiner 180, and the property determiner 190 may be implemented as one or more stand-alone applications. Further, various services and/or modules may be located on any number of servers. By way of example only, the performance property modeler 160 may reside on a server, cluster of servers, a cloud-computing device or distributed computing architecture, or a computing device remote from the known composition spectra data source 110, the compositional class data source 120, the performance property data source 130, and the computing device 150. In certain aspects, one or more services and/or modules of the performance property modeler 160 may reside in the computing device 150, such as a laptop computer, phone, and/or a tablet. In the same or alternative aspects, one or more services and/or modules of the performance property modeler 160 may reside in one or more servers, cluster of servers, cloud-computing devices or distributed computing architecture, or a computing device remote from the computing device 150.

In aspects, the composition determiner 170 can provide a model of composition. For instance, in such aspects, the composition determiner 170 receives or accesses an FT-IR spectrum for an unknown composition, e.g., via the network 140, and receives the known composition FT-IR spectra from the known composition spectra data source 110. The composition determiner 170 determines a model of composition for the unknown composition, e.g., using the processes described above that involves representing the FT-IR spectrum of the unknown composition as a weighted combination of FT-IR spectra of known compositions and generating a model of composition from this representation.

In aspects the fit quality determiner 180 can determine the fit quality of the model of composition that was provided from the composition determiner 170. In various aspects, the fit quality determiner 180 receives or accesses spectral regions of interest of the FT-IR spectrum of the unknown composition, e.g., from the compositional class data source 120. In aspects, an operator may indicate to the fit quality determiner 180 the specific spectral regions of interest, e.g., via the computing device 150. Further, the fit quality determiner 180 receives or accesses the known composition FT-IR spectra from the known composition spectra data source 110. The fit quality determiner 180 determines one or more of a combined leverage, a combined residual, and a distance as described in the PLS analysis above.

In aspects, the property determiner 190 calculates one or more performance properties of the model of composition determined by the composition determiner 170. In various aspects, the property determiner 190 receives the model of composition and optionally receives performance property information from the performance property data source 130. The property determiner 190 can calculate one or more performance properties of the model of composition as described above.

In aspects, the performance property modeler 160 can provide to an operator, e.g., via the network 140, the model of composition, fit quality information, and calculated performance properties of the model of composition.

Figure 2:
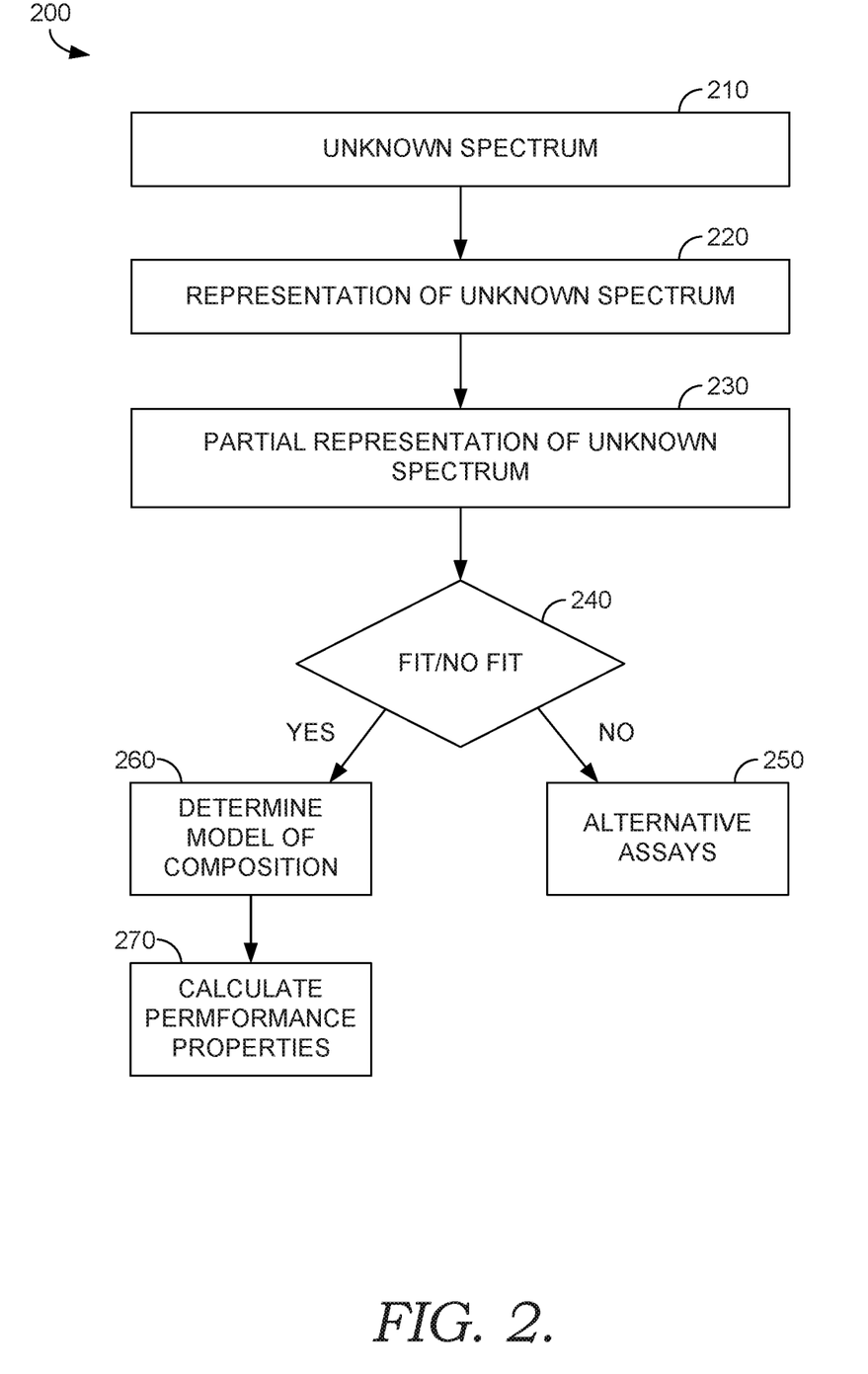
FIG. 2 shows a flow diagram illustrating processes for determining performance properties of a petroleum distillate fraction.

Turning now to FIG. 2, a flow diagram illustrating a process 200 for determining performance properties of an unknown composition is depicted. The process 200 starts with the step 210 of obtaining an FT-IR spectrum of the unknown composition. Any convenient method for obtaining an FT-IR spectrum of the unknown composition can be utilized.

In step 220, the full FT-IR spectrum of the unknown composition is represented as a weighted combination of FT-IR spectra from a database of FT-IR spectra of known compositions. In aspects, the step 220 includes the processes described in detail above that relate to developing a model of composition. As described above, based on the weighted combination of FT-IR spectra of known compositions, a model of composition is generated, which can include the relative abundance of specific classes of compounds, such as paraffins, naphthenes, olefins, and aromatics.

At step 230, partial representations of spectral regions of interest (of the FT-IR spectrum of the unknown composition) are determined. These partial representations include a weighted combination of FT-IR spectra of known compositions. In aspects, the step 230 includes the processes described in detail above for determining the fit quality of the model of composition. In one aspect, the spectral regions of interest can correlate to one or more classes of compounds, as discussed above. This step 230 (along with step 240) provides for a targeted query of the database of spectra of known compositions to determine if classes of compounds of interest are adequately represented, so that the weighted combination of spectra that is to be used to determine the model of composition can be indicated as a reliable, quality fit, or not.

In aspects, prior to the step 230, the FT-IR spectrum of the unknown composition can be preprocess to trim the FT-IR spectrum into spectral regions of interest that can be utilized in the fit quality determination. In one aspect, the FT-IR spectrum can be trimmed into regions that correspond to classes of compounds of interest, such as n-paraffins, iso-paraffins, olefins, naphthenes, total aromatics, one-ring aromatics, two-ring aromatics, three-ring aromatics, four-ring aromatics, or combinations thereof.

This step 230 can also include determining the residual and leverage values for the specific PLS models (e.g., of the wavelength sub-regions of interest). In one aspect, the residual and leverage values can be determined according to the equations (3)-(8) discussed in detail above. Further, a distance measure may be calculated based on the residual and leverage values. The distance measure can be determined utilizing the equation (9) discussed in detail above.

In step 240, a determination is made as to whether or not the representation of the FT-IR spectrum of the unknown composition of step 220 is a good fit or not for the specific spectral regions of interest. In one aspect, a combined residual ($FQR_{residual}$) of one or less and/or a combined leverage ($FQR_{leverage}$) of one or less indicates that the model composition is a good fit. In the same or alternative aspects, when the distance measure is above one, the model of composition is determined to be a bad fit.

It should be understood that the representation of the FT-IR spectrum of the unknown composition of step 220 can be performed concurrent to the steps 230 and 240 to determine the fit quality.

At step 260, if the representation of the FT-IR spectrum of the unknown composition of step 220 is a good fit for the specific spectral regions of interest, the model of composition is determined, as discussed above.

It should be understood, that in various aspects, the model of composition can be determined prior to, or concurrent with, determining the fit quality. For instance, the steps 220 and the 260 can occur, prior to, or concurrent with the steps 230 and 240.

In step 270, based on the model of composition, and the compositional profile therein, one or more performance properties are calculated, such as RON, MON, and/or cetane. In certain aspects, when the unknown composition is a naphtha boiling range composition, a light naphtha boiling range composition, or a heavy boiling range naphtha composition, the RON and/or MON can be determined as discussed above. In various aspects, when the unknown composition is a diesel boiling range composition or a jet fuel boiling range composition, the cetane number can be determined as discussed above.

At step 250 if the representation of the FT-IR spectrum of the unknown composition of step 220 is not a good fit for the specific spectral regions of interest, alternative assays, e.g., more laborious conventional models for determining the performance properties of the unknown composition can be considered.

Additional Embodiments

Embodiment 1. A method for estimating a performance property of a naphtha boiling range composition, comprising: representing an optical spectrum of a first naphtha boiling range composition as a first weighted combination of optical spectra from a library of optical spectra; generating a model of composition for the first naphtha boiling range composition based on the first weighted combination of optical spectra; and estimating a RON, MON, or both based on the model of composition.

Embodiment 2. The method of embodiment 1, further comprising: determining a first partial representation of the optical spectrum of the first naphtha boiling range composition as a second weighted combination of optical spectra from the library of optical spectra, the first partial representation being determined by partial least squares analysis, wherein the first partial representation corresponds to one or more spectral regions associated with a first compositional class, and wherein the first partial representation comprises a first leverage value and a first residual value; determining a second partial representation of the optical spectrum of the first naphtha boiling range composition as a third weighted combination of optical spectra from the library of optical spectra, the second partial representation being determined by partial least squares analysis, wherein the second partial representation corresponds to one or more spectral regions associated with a second compositional class, and wherein the second partial representation comprises a second leverage value and a second residual value; calculating a combined leverage value based on at least the first leverage value and the second leverage value; calculating a combined residual value based on at least the first residual value and the second residual value; and identifying the first weighted combination of optical spectra as having good fit quality based on the combined leverage value being one or less, the combined residual value being one or less, or a combination thereof.

Embodiment 3. The method of embodiment 2, wherein at least a portion of the generating a model of composition for the first naphtha boiling range composition and at least a portion of the identifying the first weighted combination of optical spectra as having good fit quality occur concurrently.

Embodiment 4. The method of embodiments 2 or 3, wherein each of the first compositional class and the second compositional class are selected from: n-paraffins; iso-paraffins; olefins; naphthenes; or total aromatics.

Embodiment 5. The method of embodiment 2 or 3, wherein each of the one or more spectral regions associated with the first compositional class and the one or more spectral regions associated with the second compositional class are selected from: 1) about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof; 2) about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof; 3) about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof, or 4) about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof.

Embodiment 6. The method of any of embodiments 1-5, wherein the first naphtha boiling range composition has an initial or T5 boiling point of at least about 50° F. (10° C.), and a final or T95 boiling point of 350° F. (177° C.) or more.

Embodiment 7. The method of any of embodiments 1-6, wherein the optical spectra from the library of optical spectra comprises optical spectra from at least two separate refineries, or wherein the optical spectra from the library of optical spectra comprises optical spectra from at least 50 individual known naphtha boiling range compositions.

Embodiment 8. A method for determining a performance property of a distillate fuel, comprising: representing an optical spectrum of a first distillate fuel as a first weighted combination of optical spectra from a library of optical spectra; generating a model of composition for the first distillate fuel based on the first weighted combination of optical spectra; and estimating a cetane number based on the model of composition.

Embodiment 9. The method of embodiment 8, further comprising: determining a first partial representation of the optical spectrum of the first distillate fuel as a second weighted combination of optical spectra from the library of optical spectra, the first partial representation being determined by partial least squares analysis, wherein the first partial representation corresponds to one or more spectral regions associated with a first compositional class, and wherein the first partial representation comprises a first leverage value and a first residual value; determining a second partial representation of the optical spectrum of the first distillate fuel as a third weighted combination of optical spectra from the library of optical spectra, the second partial representation being determined by partial least squares analysis, wherein the second partial representation corresponds to one or more spectral regions associated with a second compositional class, and wherein the second partial representation comprises a second leverage value and a second residual value; calculating a combined leverage value based on at least the first leverage value and the second leverage value; calculating a combined residual value based on at least the first residual value and the second residual value; and identifying the first weighted combination of optical spectra as having good fit quality based on the combined leverage value being one or less, the combined residual value being one or less, or a combination thereof.

Embodiment 10. The method of embodiment 9, wherein at least a portion of the generating the model of composition for the first distillate fuel and at least a portion of the identifying the first weighted combination of optical spectra as having good fit quality occur concurrently.

Embodiment 11. The method of embodiments 9 or 10, wherein each of the first compositional class and the second compositional class are selected from: n-paraffins; iso-paraffins; olefins; naphthenes; or total aromatics.

Embodiment 12. The method of any of embodiments 9-11, wherein each of the one or more spectral regions associated with the first compositional class and the one or more spectral regions associated with the second compositional class are selected from: 1) about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof 2) about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof 3) about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof or 4) about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof.

Embodiment 13. The method of any of embodiments 8-12, wherein the first distillate fuel comprises a diesel boiling range composition having an initial or T5 boiling point of at least about 350° F. (177° C.), and a final or T95 boiling point of less than about 650° F. (343° C.); or wherein the first distillate fuel comprises a jet fuel boiling range composition having an initial or T5 boiling point of at least about 284° F. (140° C.), and a final or T95 boiling point of less than about 572° F. (300° C.).

Embodiment 14. The method of any of embodiments 8-13, wherein the optical spectra from the library of optical spectra comprises optical spectra from at least two separate refineries, or wherein the optical spectra from the library of optical spectra comprises optical spectra from: at least 50 individual known diesel boiling range compositions; 50 individual known jet fuel boiling range compositions; or a combination thereof.

Embodiment 15. The method of any of the above embodiments, wherein the optical spectrum comprises an FT-IR spectrum.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

The invention claimed is:

1. A method for estimating a performance property of a first unknown naphtha boiling range composition using a system having a performance property modeler, a known composition spectra data source, a compositional class data source and a computing device operatively connected through a network, wherein the performance property modeler includes a composition determiner, a fit quality determiner and a property determiner, comprising, comprising:

obtaining an optical spectrum for the first unknown naphtha boiling range composition;

representing the optical spectrum of the first unknown naphtha boiling range composition as a first weighted combination of optical spectra from a library of optical spectra from the known composition spectra data source;

generating a model of composition for the first naphtha boiling range composition using the composition determiner of the performance property modeler based on the first weighted combination of optical spectra;

determining a first partial representation of the optical spectrum of the first naphtha boiling range composition as a second weighted combination of optical spectra from the library of optical spectra from the known composition spectra data source, the first partial representation being determined by partial least squares analysis, wherein the first partial representation corresponds to one or more spectral regions associated with a first compositional class from the compositional class data source, and wherein the first partial representation comprises a first leverage value and a first residual value;

determining a second partial representation of the optical spectrum of the first naphtha boiling range composition as a third weighted combination of optical spectra from the library of optical spectra from the known composition spectra data source, the second partial representation being determined by partial least squares analysis, wherein the second partial representation corresponds to one or more spectral regions associated with a second compositional class from the compositional class data source, and wherein the second partial representation comprises a second leverage value and a second residual value;

calculating a combined leverage value based on at least the first leverage value and the second leverage value;

calculating a combined residual value based on at least the first residual value and the second residual value;

identifying the first weighted combination of optical spectra as having good fit quality based on the combined leverage value being one or less, the combined residual value being one or less, or a combination thereof, wherein at least a portion of the generating a model of composition for the first naphtha boiling range composition and at least a portion of the identifying the first weighted combination of optical spectra as having good fit quality occur concurrently determined using the fit quality determiner of the performance property modeler with data obtained from the compositional class data source; and estimating a Research Octane Number (RON), Motor Octane Number (MON), or both based on the model of composition obtained from the composition determiner using the property determiner of the performance property modeler.

2. The method of claim 1, wherein each of the first compositional class and the second compositional class are selected from: n-paraffins; iso-paraffins; olefins; naphthenes; or total aromatics.

3. The method of claim 1, wherein each of the one or more spectral regions associated with the first compositional class and the one or more spectral regions associated with the second compositional class are selected from: 1) about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof; 2) about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof; 3) about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof; or 4) about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof.

4. The method of claim 1, wherein the first naphtha boiling range composition has an initial or T5 boiling point of at least about 50° F. (10° C.), and a final or T95 boiling point of 350° F. (177° C.) or more.

5. The method of claim 1, wherein the optical spectrum of the first naphtha boiling range composition comprises an FT-IR spectrum.

6. The method of claim 1, wherein the optical spectra from the library of optical spectra comprises optical spectra from at least two separate refineries.

7. The method of claim 1, wherein the optical spectra from the library of optical spectra comprises optical spectra from at least 50 individual known naphtha boiling range compositions.

* * * * *